(12) United States Patent
Taneff (10) Patent No.: US 9,030,325 B2
(45) Date of Patent: May 12, 2015

(54) HAND WASHING ENFORCEMENT SYSTEM (76) Inventor: Yordan Gineff Taneff, Lantana, FL (US)

( * ) Notice: Subject to any disclaimer, the term of this patent is extended or adjusted under 35 U.S.C. 154(b) by 0 days.

(21) Appl. No.: 13/200,130

(22) Filed: Sep. 19, 2011

(65) Prior Publication Data
US 2012/0062382 A1 Mar. 15, 2012

Related U.S. Application Data (63) Continuation-in-part of application No. 12/873,870, filed on Sep. 1, 2010, now abandoned.

(60) Provisional application No. 61/275,582, filed on Sep. 1, 2009.

(51) Int. Cl.
G08B 23/00 (2006.01)
G08B 21/24 (2006.01)
G06F 19/00 (2011.01)

(52) U.S. Cl.
CPC ............ *G08B 21/245* (2013.01); *G06F 19/327* (2013.01)

(58) Field of Classification Search
USPC ............ 340/539.11, 541, 573.1, 539, 539.13, 340/572.1, 539.12, 5.81
See application file for complete search history.

(56) References Cited

U.S. PATENT DOCUMENTS

| 5,202,666 A | 4/1993 | Knippscheer | |
|---|---|---|---|
| 8,547,220 B1 * | 10/2013 | Dempsey et al. | 340/539.12 |
| 8,587,437 B2 * | 11/2013 | Kyle et al. | 340/573.1 |
| 2004/0090333 A1 * | 5/2004 | Wildman et al. | 340/573.1 |
| 2005/0134465 A1 * | 6/2005 | Rice et al. | 340/573.1 |
| 2007/0080801 A1 | 4/2007 | Weismiller et al. | |
| 2007/0096930 A1 | 5/2007 | Cardoso | |
| 2007/0257803 A1 * | 11/2007 | Munro et al. | 340/573.1 |
| 2008/0001763 A1 * | 1/2008 | Raja et al. | 340/573.1 |
| 2008/0087719 A1 | 4/2008 | Sahud | |
| 2008/0131332 A1 | 6/2008 | Nguyen et al. | |
| 2008/0246599 A1 * | 10/2008 | Hufton et al. | 340/529 |
| 2009/0051545 A1 | 2/2009 | Koblasz | |
| 2009/0091458 A1 | 4/2009 | Deutsch | |
| 2009/0189759 A1 | 7/2009 | Wildman et al. | |
| 2009/0224907 A1 * | 9/2009 | Sinha et al. | 340/539.11 |
| 2009/0237254 A1 * | 9/2009 | Munro et al. | 340/572.1 |
| 2010/0117823 A1 * | 5/2010 | Wholtjen | 340/539.13 |
| 2010/0117836 A1 * | 5/2010 | Seyed Momen et al. | 340/573.1 |
| 2010/0123560 A1 * | 5/2010 | Nix et al. | 340/10.4 |
| 2010/0134296 A1 | 6/2010 | Hwang | |
| 2010/0173581 A1 * | 7/2010 | Dolan | 455/39 |
| 2010/0265059 A1 * | 10/2010 | Melker et al. | 340/539.11 |
| 2010/0328076 A1 * | 12/2010 | Kyle et al. | 340/573.1 |
| 2011/0057799 A1 * | 3/2011 | Taneff | 340/573.1 |
| 2011/0068930 A1 * | 3/2011 | Wildman et al. | 340/573.1 |
| 2011/0121974 A1 * | 5/2011 | Tenarvitz et al. | 340/573.1 |
| 2011/0206378 A1 * | 8/2011 | Bolling et al. | 398/108 |
| 2011/0227740 A1 * | 9/2011 | Wohltjen | 340/573.1 |
| 2011/0254682 A1 * | 10/2011 | Sigrist Christensen | 340/539.12 |
| 2012/0062382 A1 * | 3/2012 | Taneff | 340/573.1 |
| 2012/0194338 A1 * | 8/2012 | Snodgrass | 340/539.12 |
| 2013/0027199 A1 * | 1/2013 | Bonner | 340/539.11 |

* cited by examiner

Primary Examiner — Hoi Lau
(74) Attorney, Agent, or Firm — Malloy & Malloy, P.L.

(57) ABSTRACT

A hand cleansing monitoring system that electronically monitors and communicates hand washing frequency and procedures to management through a computer based system.

24 Claims, 9 Drawing Sheets

| Activities | RF-ID | RF-DU | RF-AU |
|---|---|---|---|
| Employee entering restroom | ❖ ID wakes up<br>❖ ID < time stamp<br>❖ ID > info: name | ❖ Interrogates the ID<br>❖ DU > time stamp<br>❖ DU < info: name<br>❖ DU > LCD welcome message<br>❖ DU > audio welcome message | |
| | ❖ ID starts duration timers | | |
| Employee inside restroom | ❖ ID maintains the duration timers<br>❖ ID flashes LED orange | ❖ DU resets | |
| Employee approaches sink | | | ❖ AU detects the ID within the engagement distance<br>❖ AU engages ID |
| | ❖ ID constantly acknowledges its presence | | ❖ AU constantly interrogates ID |
| Hand washing process | ❖ Employee is monitored while following the steps. Monitoring is done via complex sensing algorithm.<br>❖ ID alternates LED green/red | | ❖ AU starts hand washing process step by step:<br>• Soap dispensing,<br>• Hand rubbing + low water<br>• Rinsing + high water flow |
| If process is successfully completed | ❖ ID is stamped with pass<br>❖ ID flashes LED green | | ❖ AU stamps ID with pass<br>❖ AU > LCD thanks message<br>❖ AU > audio thanks message |
| | ❖ Employee may leave restroom | | ❖ AU resets |
| If process is interrupted | ❖ ID is stamped with fail<br>❖ ID flashes LED red | | ❖ AU stamps ID with fail<br>❖ AU > LCD warning message<br>❖ AU > audio warning message |
| | ❖ Employee may start the hand washing over | | ❖ AU awaits ID |
| Employee leaving restroom | ❖ ID > info: name +time stamps<br>❖ ID > pass/fail status | ❖ DU < info: name +time stamps<br>❖ DU < pass/fail status | |
| If passed | ❖ ID flashes LED green for 30 seconds | ❖ DU > LCD thanks message<br>❖ DU > audio thanks message<br>❖ DU > flashes LED green | |
| | ❖ Employee leave the area | ❖ DU resets | |
| If failed | ❖ ID flashes LED red for 20 minutes | ❖ DU > LCD warning message<br>❖ DU > audio warning message<br>❖ DU > flashes LED red | |
| | ❖ Employee should reenter restroom to wash again | ❖ DU acknowledges ID reentry | |
| At the end of the day | ❖ ID resets | ❖ DU upload history files<br>❖ DU resets | ❖ AU resets |

*FIG. 9*

HAND WASHING ENFORCEMENT SYSTEM

CROSS REFERENCE TO RELATED APPLICATIONS

This application is a continuation-in-part of non-provisional patent application Ser. No. 12/873,870 filed on Sep. 1, 2010, which claims priority to provisional patent application having Ser. No. 61/275,582 filed on Sep. 1, 2009, all of the contents of which are incorporated by reference herein in their entireties.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of Invention

This invention is in the field of healthcare, food processing, foodservice, and other industries and is related to maintaining proper hygiene at any work environment. It is an electronic hand-washing monitoring and enforcing system that will be installed at restroom areas as well as all other areas requiring proper hand washing in the healthcare, food processing, foodservice, and other facilities, such as restaurants, hospitals, hotels, and others. The system uses RFID(s) (Radio Frequency Identification Unit) communicating with other electronic units through the use of RF waves in order to achieve its main objective, i.e. proper hygiene. A main database including every individual's specific data in regard to his/her compliance with hand-washing requirements is maintained in a central computer for the management to review.

2. Background of the Invention

Both monitoring hand washing through the use of RF (radiofrequency) technology and the use of mobile RF units as agents of transfer of information from one RF unit to another, as well as to a computer data base, are well known activities in prior art. The combination of said two activities, together with the monitoring of the hand rubbing techniques as called for in the Preferred Embodiment #2 for the purpose of monitoring hand washing, however, has never been mentioned in prior art. My extensive research in the USPTO's and Delphion's databases for patents issued since 1971 and in the Patent and Trademark Depository Library in Ft. Lauderdale, Fla., did not uncover any reference with regard to said combination, i.e. others have failed to come up with it. While monitoring hand washing as taught by prior art is theoretically possible, the use of said combination makes it practicable to achieve at an affordable price. As a matter of fact we have developed a unit, ready for mass production, whose cost per unit installed will be in the range of $300.00 to $500.00. Said combination does solve "long but unsolved need"—the need to minimize the spread of infections to patients in hospitals, as well as to employees, and the general public at large at a price that will avoid placing an undue burden to businesses. Hospital acquired infections cause the premature deaths of 100,000 patients per year in the United States alone (and 2,000,000 or more worldwide) and extended hospital stays of 2,000,000 patients per year in the United States (and 40,000,000, or more worldwide). The end result, after reducing the number of deaths, and extended hospital stays from hospital acquired infections, will be a reduction of hospital costs per patient, as well as a reduction in hospital insurance premiums. Hospitals, as well as other enterprises will end up saving money by using my invention. Also, having in mind that my invention will result in almost 100% compliance with proper hand-washing at the workplace, compared with the 30% or less presently when left up to the conscientiousness of the individual employee, said combination does produce "new and unexpected results" and does achieve "results greater than the sum of its parts". Yet another major difference between the teachings in prior art and mine is that, while prior art teaches that monitoring of hand washing within a hospital setting could be achieved by monitoring the specific location of employees, patients, and equipment at any given time through the use of constant communication with a Master Station, whose analytical power determines compliance or non-compliance with hand washing and provides statistical analysis, I teach that the same could be achieved by chance encounters with patients or contaminated objects, where the determination of compliance or non-compliance with hand washing is being achieved by using the analytical power of the RFID (radiofrequency identification unit) worn by the employee, and the Computer Data Base only rearranges the data in a format that is easy to review by the management. Yet another major difference between the teachings in prior art and mine is that, while prior art teaches that monitoring of hand washing is being achieved through the use of long range RF transmissions from any RF unit located within the hospital to a master station, I teach that the same is being achieved through the use of short range RF transmissions with a radius of transmission no greater than two to four feet. Yet another major difference between the inventions discussed in prior art and mine is that my invention teaches how to monitor specific hand rubbing techniques required by Centers for Disease Control and Prevention (CDC) and World Health Organization (WHO), which could be found at the following link: http://www.who.int/gpsc/5may/How_To_HandRub_Poster.pdf Infections, germs, viruses, such as Hepatitis A, and other infections are spread through ingesting food or drinks handled by a person whose hands are contaminated. So, employees in the food service industry or medical industry, who either do not wash their hands or improperly wash their hands after using rest room facilities or handling unsterilized objects, are the main agents of transfer of that and other types of infections to patients and to the general population. According to Center for Disease Control, hand washing is the single most important means of preventing the spread of infection and disease. Nationally, it is estimated that food borne illness kills 5,000 people a year and 5 million more become ill. Washing hands correctly will greatly reduce chances of spreading germs and can reduce food borne illnesses, which add to health care costs in excess of $4 billion a year in the U.S. All of this could be prevented by having the infected person properly wash his or her hands. Information on the subject matter from different governmental sources, food, health care industries, etc., are too numerous to present in a patent application and could be obtained on the Internet or in a library.

If there existed a system that reduced the transfer of germs, bacteria and infections, it would result in a reduction of illnesses and deaths, healthcare expenditures and hospital costs, as well as a reduction in hospital insurance premiums. The additional healthcare cost per year in the US alone is estimated to be in excess of 30 Billion dollars. An electronic system that could monitor and promote compliance with proper hand-washing requirements at the workplace would be very well received. However, there are no systems known that adequately and reliably monitor employee hand washing in restaurants or hospitals or other places where clean hands are a necessity. Therefore, there exists a need for an electronic microcontroller based hand washing monitoring system that would promote proper hand washing practices in restaurants, hospitals, schools or other places where clean hands are a necessity to prevent the spread of germs, bacteria and infections. It is, therefore, to the effective resolution of the aforementioned problems and shortcomings of the prior art that the present invention is directed. The instant invention addresses this unfulfilled need in the prior art by providing an electronic hand washing system as contemplated by the instant invention disclosed herein.

BRIEF SUMMARY OF THE INVENTION

In light of the foregoing, it is an object of the present invention to provide a hand washing monitoring system that reliably monitors and enforces whether employees actually wash their hands.

It is a further object of the instant invention to have employees or other individuals use proper hygiene at their place of employment or visit.

It is also an object of the instant invention to provide an electronic hand washing monitoring system that reliably monitors whether employees actually wash their hands.

It is another object of the instant invention to provide a hand washing monitoring system that reliably monitors whether employees actually wash their hands, and that is adapted for use in the restaurant, hospital, school environments, and others.

It is an additional object of the instant invention to provide a hand washing monitoring system that uses RFID.

It is yet another object of the instant invention to provide a hand washing monitoring system that is computer and microcontroller based.

It is yet an additional object of the instant invention to provide a hand washing monitoring system that is reliable and cost effective.

It is yet another object of the instant invention to provide a hand washing monitoring system that monitors specific hand rubbing techniques required by the Centers for Disease Control and Prevention (CDC) and the World Health Organization (WHO), which could be found at the following link: http://www.who.int/gpsc/5may/How_To_HandRub_Poster.pdf It is yet a further object of the instant invention to provide a hand washing monitoring system that records the actual duration, and process of hand washing in order to enable evaluation of employees' hand washing practices.

In light of these and other objects, the instant invention comprises an electronic hand washing monitoring system for use in restaurants, hospitals and other locations where hand cleansing is necessary in order to avoid the spread of germs, bacteria and infections. The instant invention comprises an electronic system in the field of healthcare, food processing, food service, and other industries where clean hands are a necessity. It is an electronic hand-washing monitoring system that may be installed in restrooms, sensitive hospital areas and other areas requiring proper hand washing practices. The instant invention is an RFID (Radio Frequency Identification) unit(s) based system comprising sensors, and electronic units that receive, and transmit RF signals. Said signals are processed by the microcontroller of said RFID, in order to determine whether an employee has actually washed his/her hands. Washing habits are also processed by the instant invention to achieve the main objective of advancing proper hygiene practices. A main database including every individual's specific data in regard to his/her compliance with hand-washing requirements is maintained in a central computer for the management and governmental authorities to review and analyze.

A significant difference between the teachings in prior art and the instant invention is that known systems track tendencies and not actual hand washing sessions. Known systems are not able to record and process every hand washing activity in detail. The instant invention comprises a system that monitors all hand washing activities, including dispensation of the cleansing substance, and the duration of hand rubbing and hand rinsing, in order to determine the compliance or non-compliance with hand washing requirements. The instant invention achieves its objectives by using RFID (radiofrequency identification unit) attached to each employee. The instant invention includes a computer database that rearranges the data in a format that is convenient to review and analyze by the management. Another major difference between the teachings in prior art and instant invention is that the monitoring of hand washing is being achieved through the use of short range RF transmissions, such as with a radius of transmission from two to four feet.

The instant invention provides a quantitatively improved analysis that is used in preventing the spread of disease to patients in hospitals, employees, and the general population. Prior to the instant invention proper hygiene at the work place was left up to the conscience of the employees. The instant invention gives management a tool to supervise proper hygiene practices in accordance with required protocol.

One of the main objectives achieved by the instant invention is the monitoring of employees to determine if they properly washed their hands after using a rest room facility or touching an unsterilized object prior to performing their duties. One of the main advantages of the instant invention is that it provides the ability of both management of any establishment and overseeing governmental authorities to monitor employees' proper hygiene at work remotely just by checking the data entered into a computer data base. That will improve the monitoring capability of a company management and government employees alike, both quantitatively and qualitatively. Also, another major improvement of the health of the general population could be achieved if and when the use of my invention becomes codified nationwide in the United States and abroad.

In accordance with these and other objects, which will become apparent hereinafter, the instant invention will now be described with particular reference to the accompanying drawings.

DRAWINGS

Figures

FIG. 9 is a diagram illustrating the theory of operation the alternative embodiment of the instant invention.

DRAWINGS

Reference Numerals

Figure 1:
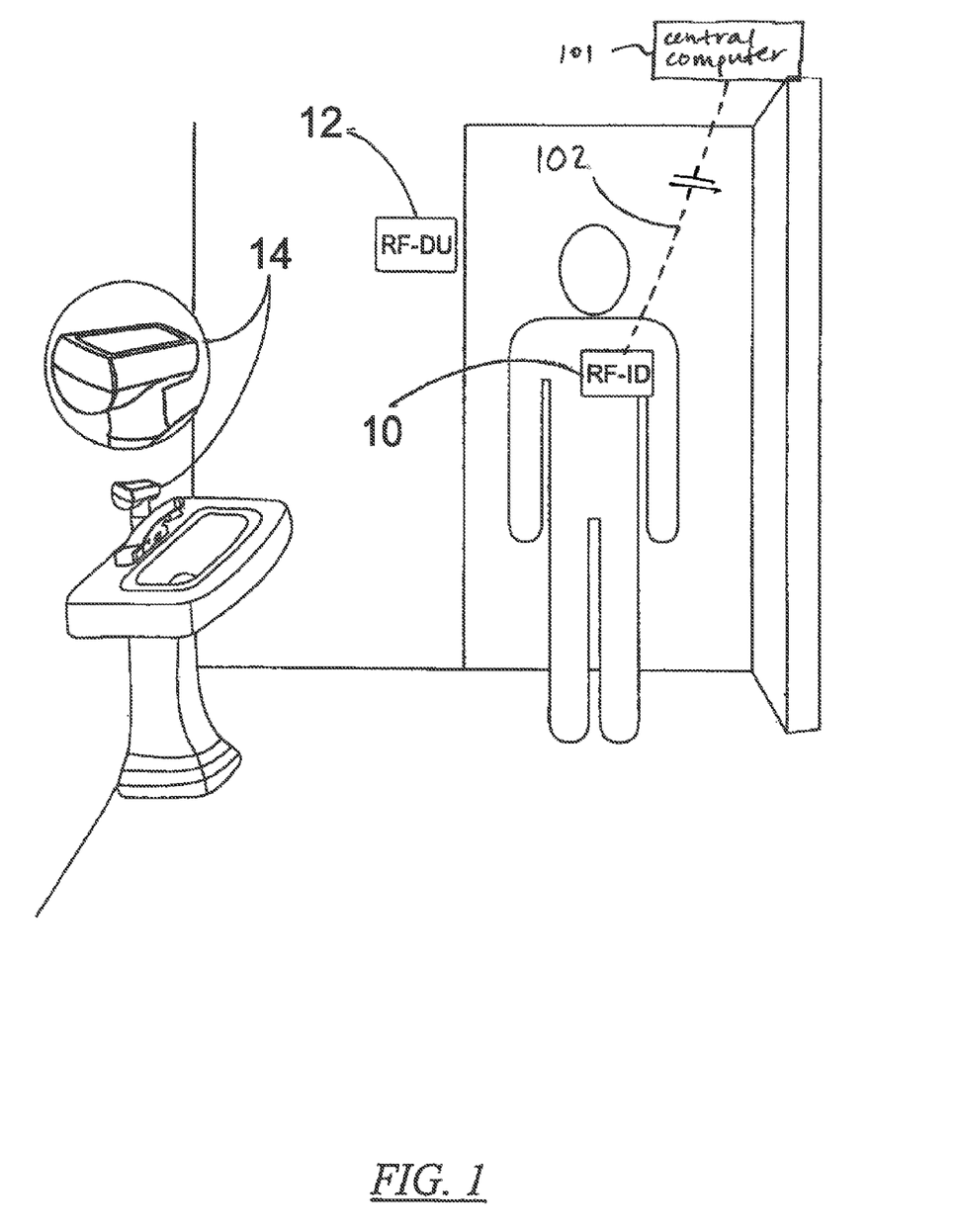
FIG. 1 is an illustrative view of the main units, RFID (radiofrequency identification unit), RFDU (radiofrequency door unit), RFSU (radiofrequency sanitation unit) and central computer, of an embodiment of the instant invention. The preferred embodiments operate on the same principle, just that the door unit could be installed both, at a restroom(s) door, and at a main entrance(s) door of a facility.
Figure 2:
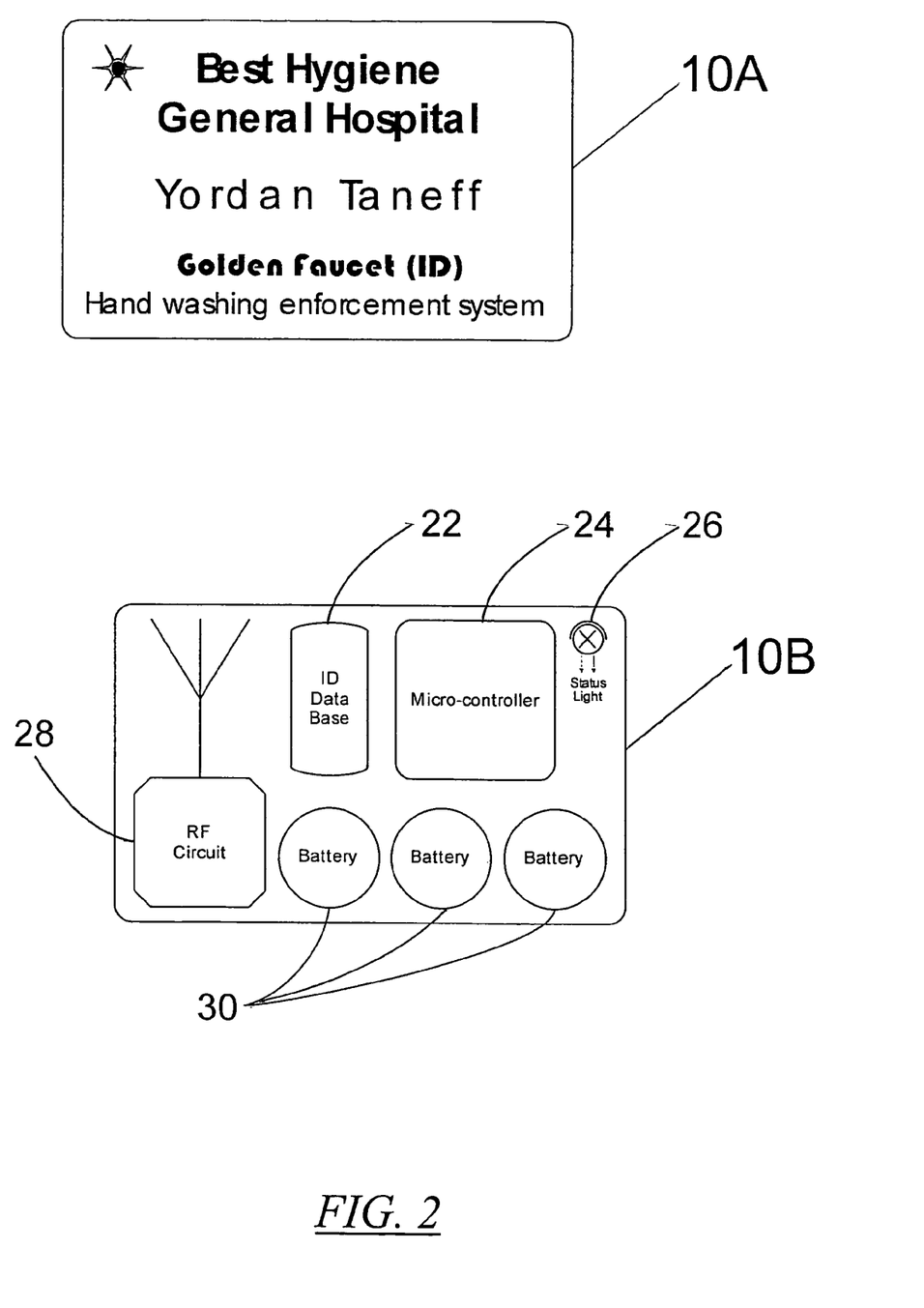
FIG. 2 is a diagrammatic view of the electronic components of the RFID (radiofrequency identification unit) of the alternative and preferred embodiments, and the RFPU (radiofrequency patient unit) of the preferred embodiment #2 only. While the electronic components of RFID, and RFPU, are identical, RFID, and RFPU, differ in functionality.
Figure 3:
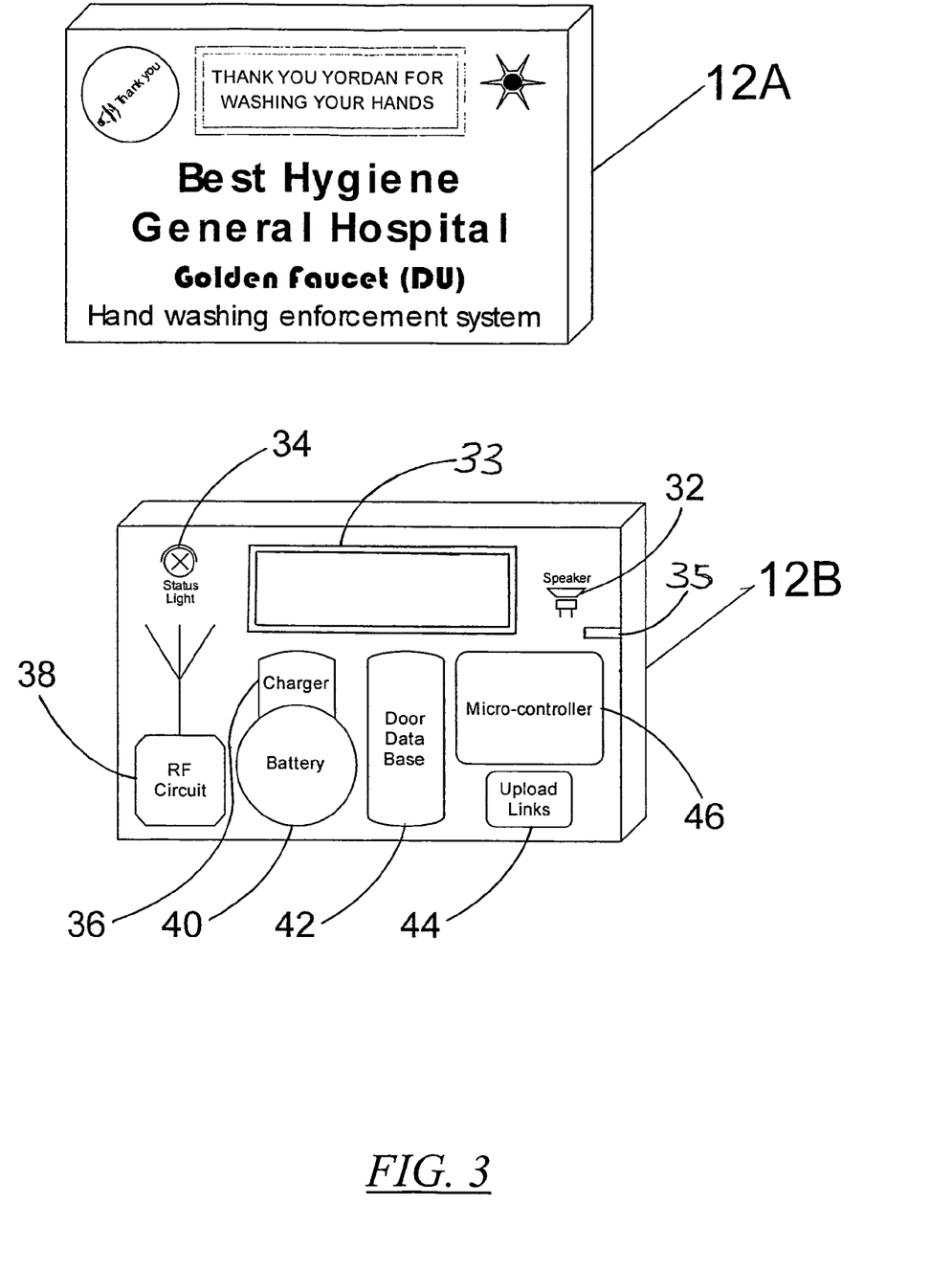
FIG. 3 is a diagrammatic view of the electronic components of the RFDU (radiofrequency door unit) for the alternative and preferred embodiments of the instant invention.
Figure 4:
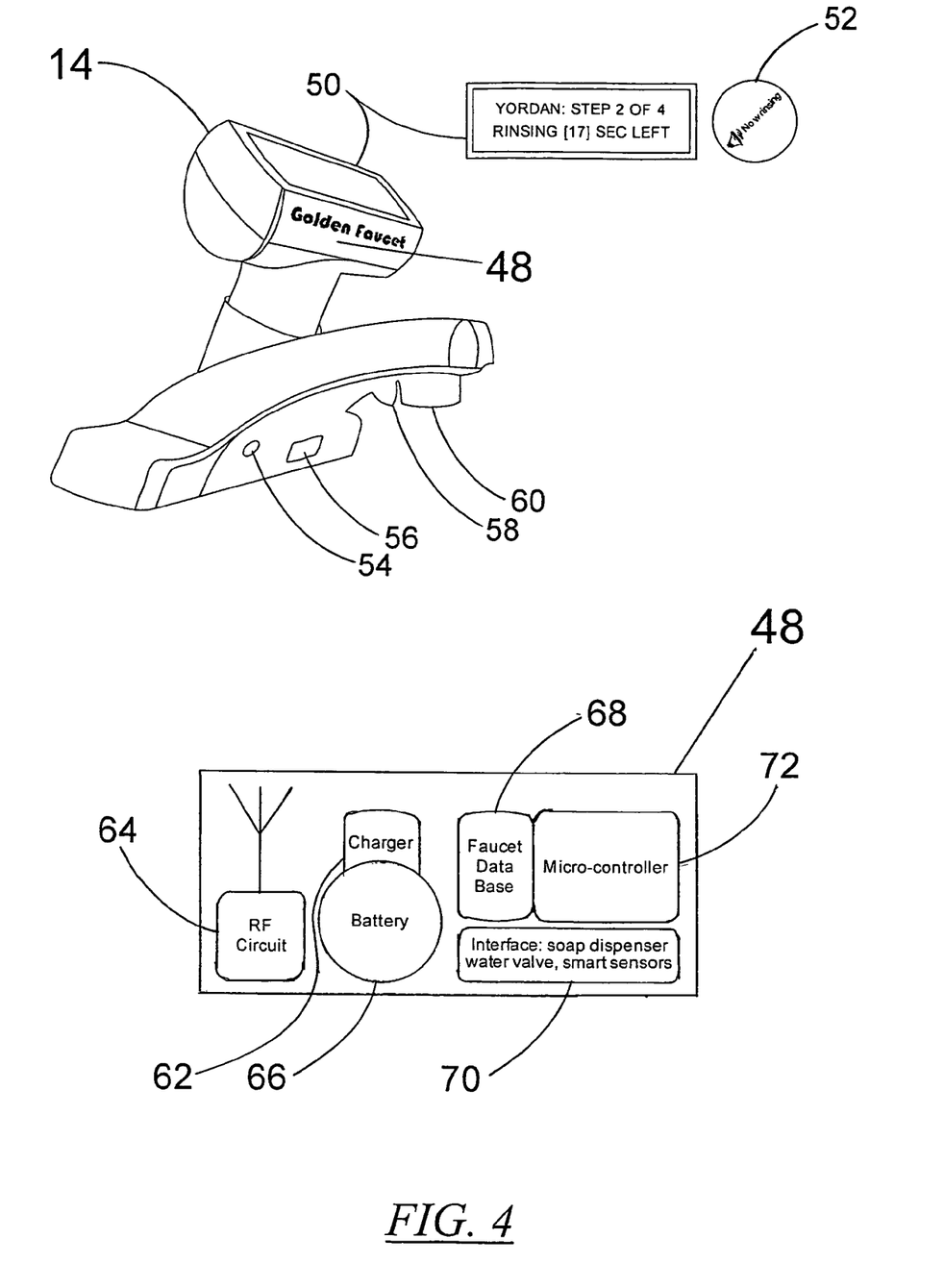
FIG. 4 is a diagrammatic view of the electronic components of the RFSU-1 (radiofrequency sanitization unit-1) for the alternative and preferred embodiments of the instant invention.
Figure 5:
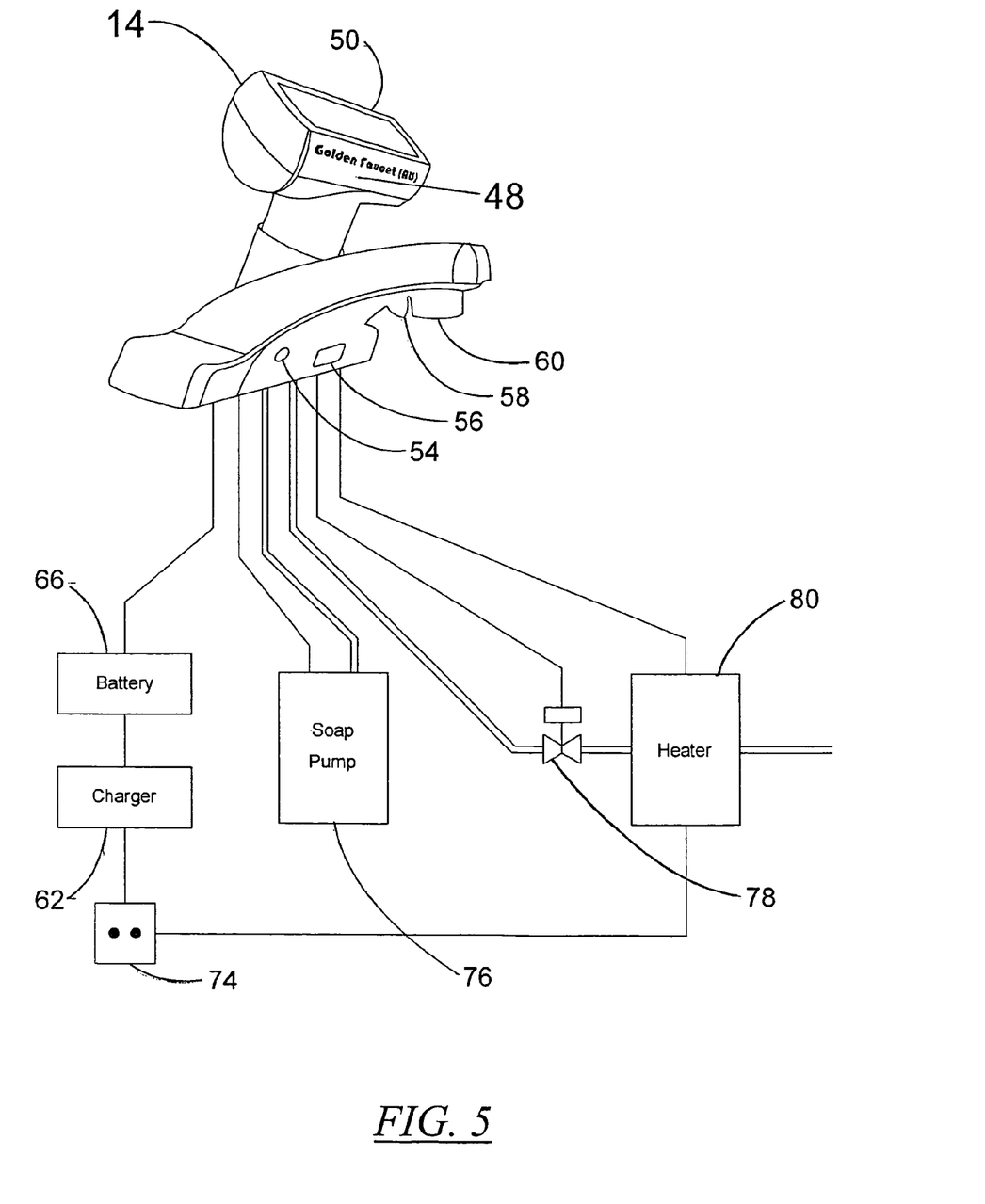
FIG. 5 is a diagrammatic view of the peripheral components of RFSU-1 (radiofrequency sanitization unit-1) for the alternative and preferred embodiments of the instant invention.
Figure 6:
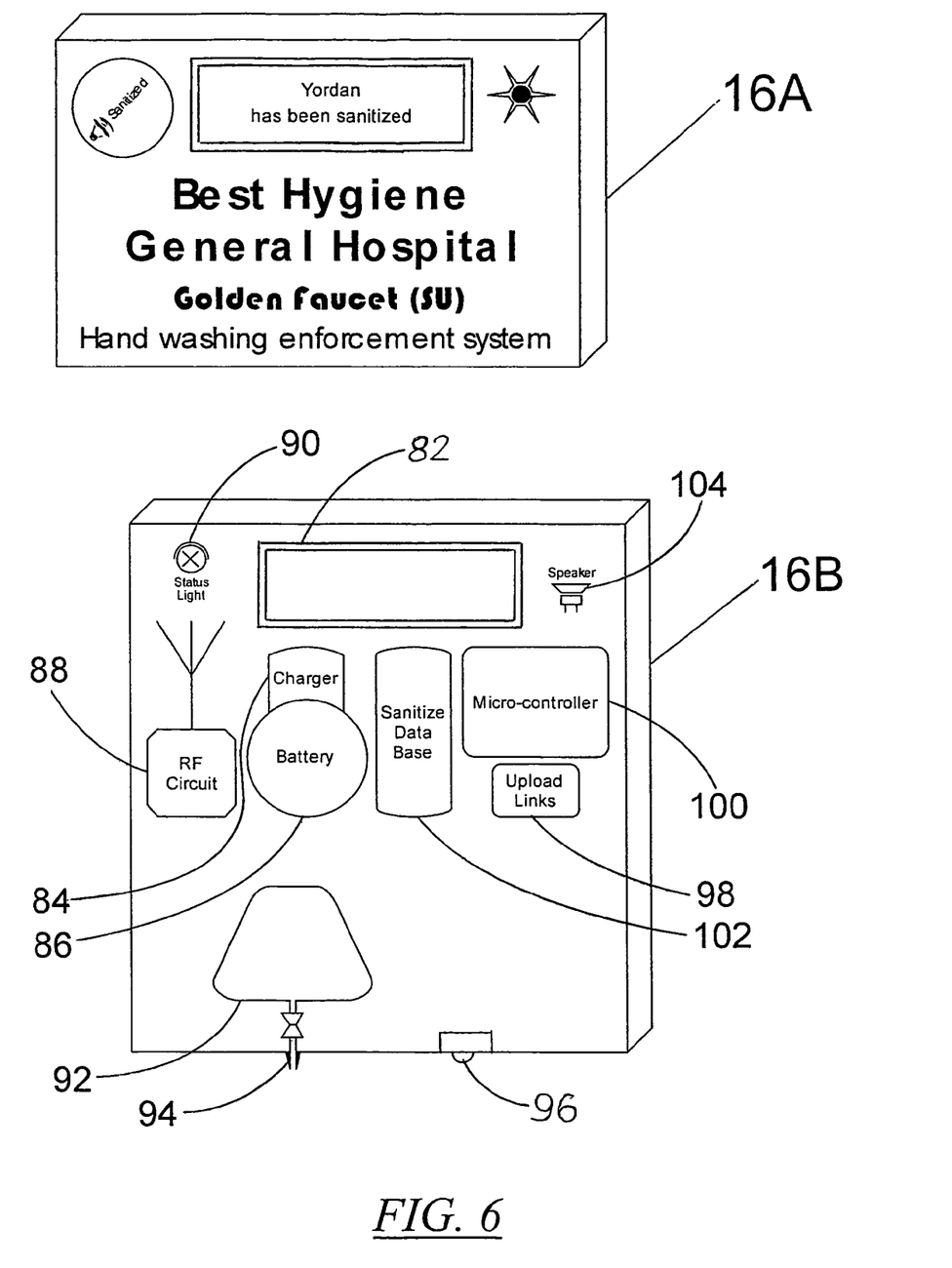
FIG. 6 is a diagrammatic view of the electronic components RFSU-2 (radiofrequency sanitization unit-2) for the alternative and preferred embodiments of the instant invention.
Figure 7:
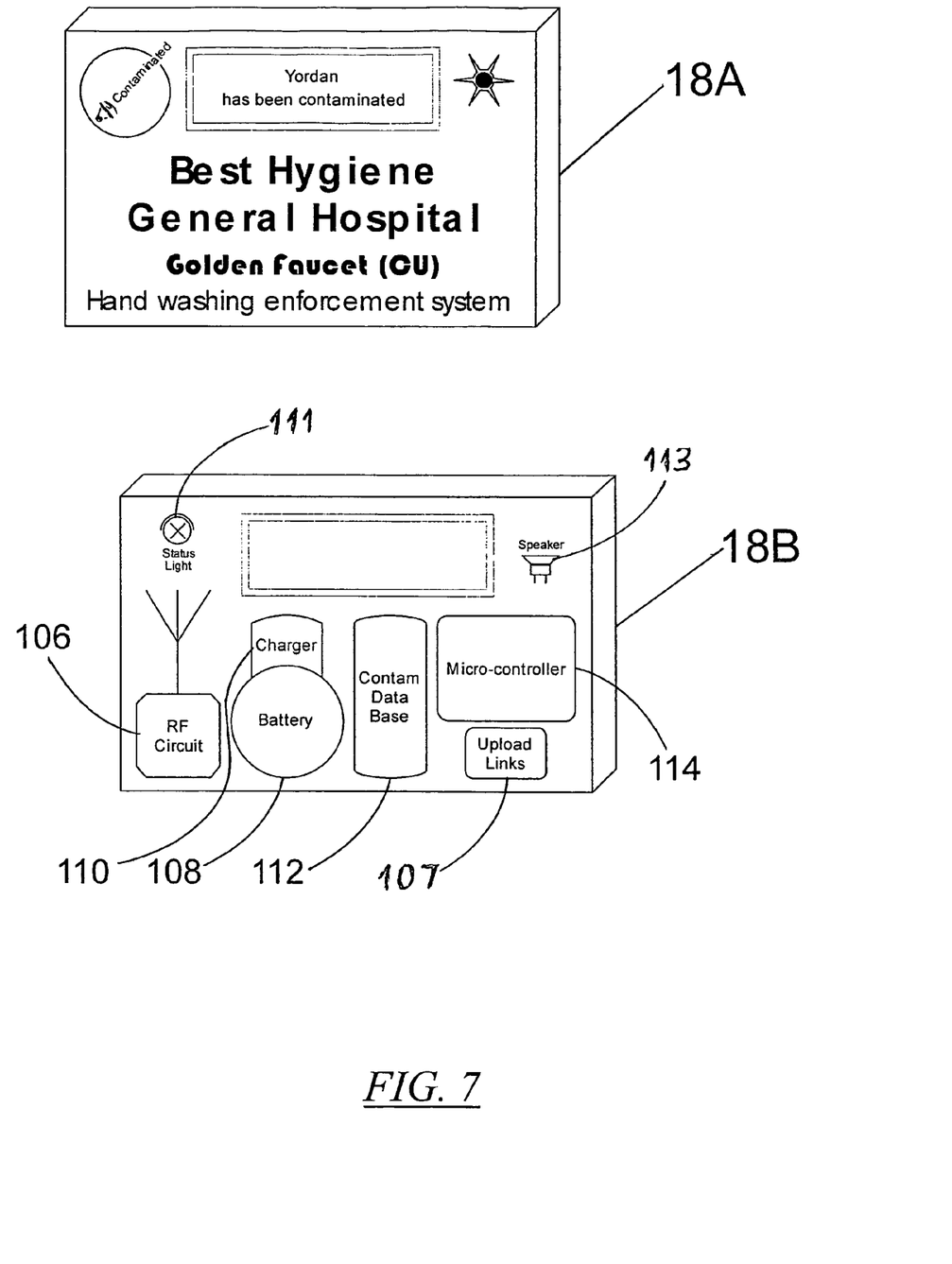
FIG. 7 is a diagrammatic view of the electronic components of RFCU-1 (radiofrequency contamination unit-1) of the preferred embodiment #1, and RFBU (radiofrequency bed unit) of the preferred embodiment #2 of the instant invention. While the electronic components of RFID, and RFPU, are identical, RFID, and RFPU, differ in functionality.
Figure 8:
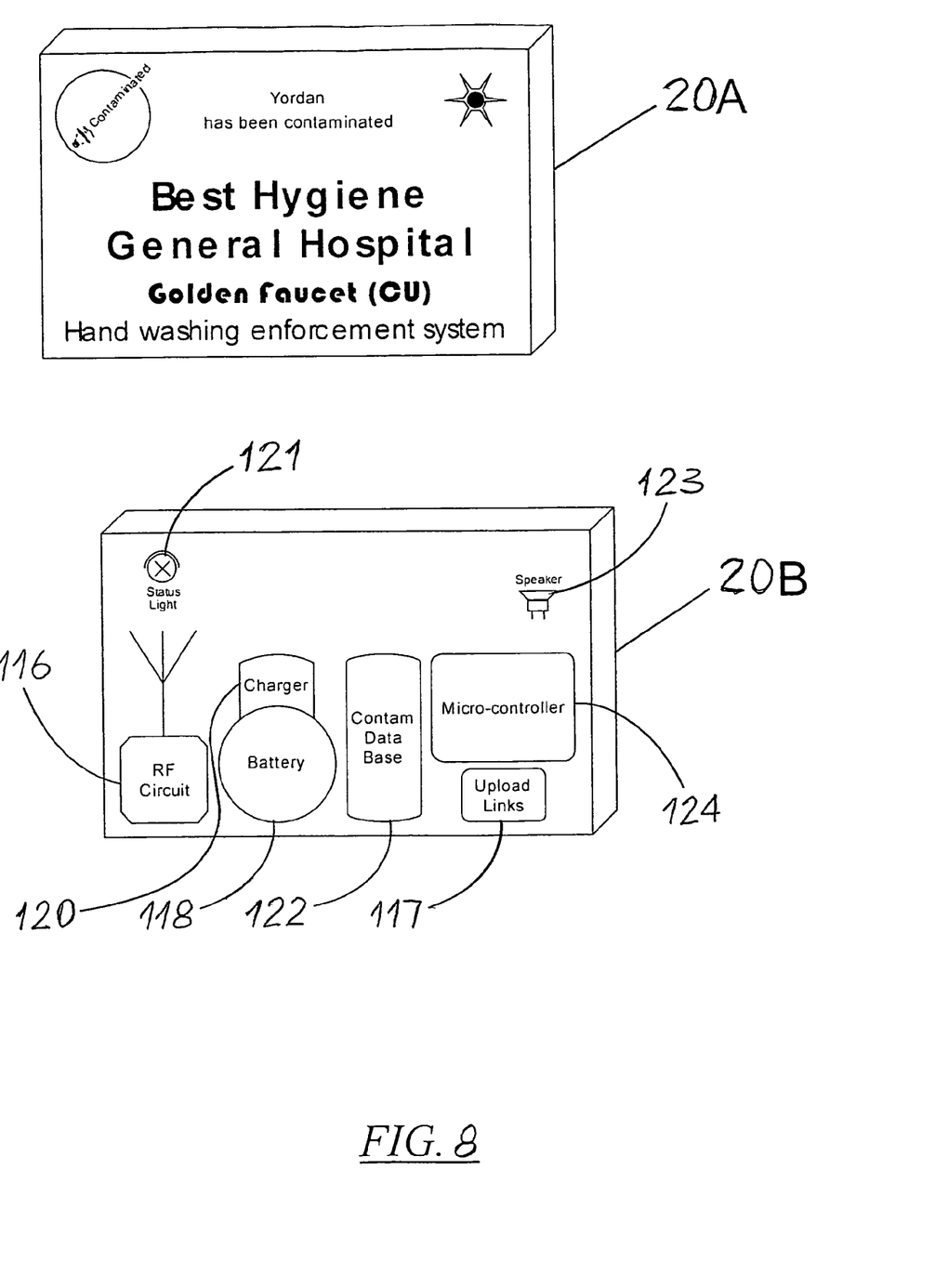
FIG. 8 is a diagrammatic view of the electronic components of RFCU-2 (radiofrequency contamination unit-2) for the preferred embodiments of the instant invention.

Reference numerals for FIG. 1:
10—RFID (radiofrequency identification unit)
12—RFDU (radiofrequency door unit)
14—RFSU 1 (radiofrequency sanitization unit 1)
101—central computer
102—hand washing activity data
Reference numerals for FIG. 2
10—RFID (radiofrequency identification unit)
22—RFID data base
24—RFID microcontroller
26—RFID status light
28—RFID radiofrequency circuit
30—RFID battery
Reference numerals for FIG. 3
12—RFDU (radiofrequency door unit)
32—RFDU speaker
33—RFDU LCD (liquefied crystal display)
34—RFDU status light
35—RFDU entry/exit sensors
36—RFDU battery charger
38—RFDU radiofrequency circuit
40—RFDU battery
42—RFDU data base
44—RFDU upload links
46—RFDU microcontroller
Reference numerals for FIGS. 4 and 5
14—PCB for RFSU-1 [embedded in faucet (48)]
48—RFSU-1 faucet
50—RFSU-1 LCD (liquefied crystal display)
52—RFSU-1 speaker
54—RFSU-1 motion sensor
56—RFSU-1 motion detector
58—RFSU-1 cleaning substance dispenser spout
60—RFSU-1 water spout
62—RFSU-1 battery charger
64—RFSU-1 radiofrequency circuit
66—RFSU-1 battery
68—RFSU-1 data base
70—RFSU-1 interface
72—RFSU-1 microcontroller
74—RFSU-1 power supply
76—RFSU-1 cleaning substance dispenser
78—RFSU-1 electric valve
80—RFSU-1 tankless water heater
Reference numerals for FIG. 6
16—PCB for RFSU-2 (radiofrequency activation unit 2)
82—RFSU-2 LCD (liquefied crystal display)
84—RFSU-2 battery charger
86—RFSU-2 battery
88—RFSU-2 radiofrequency circuit
92—RFSU-2 cleaning substance dispenser
94—RFSU-2 motion sensor
96—RFSU-2 motion detector
98—RFSU-2 interface
100—RFSU-2 microcontroller
102—RFSU-2 data base
104—RFSU-2 speaker
Reference numerals for FIG. 7
18—RFCU-1 (radiofrequency contamination unit 1)
106—RFCU-1 radiofrequency circuit
107—RFCU-1 upload link
108—RFCU-1 battery
110—RFCU-1 battery charger
111—RFCU-1 status light
112—RFCU-1 data base
113—RFCU-1 speaker
114—RFCU-1 microcontroller
Reference numerals for FIG. 8
20—RFCU-2 (Radio Frequency Contamination Unit 2)
116—RFCU-2 radiofrequency circuit
117—RFCU-2 upload link
118—RFCU-2 battery
120—RFCU-2 battery charger
121—RFCU-2 status light
122—RFCU-2 data base
123—RFCU-2 speaker
124—RFCU-2 microcontroller

DETAILED DESCRIPTION

Note: Following is a description of two preferred embodiments, #1 and #2, and an alternative embodiment. For logistical purposes the alternative embodiment is described first.

Alternative Embodiment

A fully functional prototype, ready for mass production, exists of this embodiment.

The alternative embodiment monitors proper hand washing in a restroom and consists of three main units and one optional unit (see FIGS. 1, 2, 3, 4, 5, and 6):
1. RFID [radiofrequency identification unit (10)—see FIG. 2]. The main building blocks of RFID are:
   a. RFID microcontroller (24)
   b. RFID radiofrequency circuit (28)

c. RFID data base (28)
d. RFID battery (30)
e. RFID status light (26)
2. RFDU [radiofrequency door unit (12)—see FIG. 3]. The main building blocks of RFDU are:
   a. RFDU microcontroller (46)
   b. RFDU radiofrequency circuit (38)
   c. RFDU data base (42)
   d. RFDU battery (40)
   e. RFDU battery charger (36)
   f. RFDU upload links (44)
   g. RFDU speaker (32)
   h. RFDU LCD (liquefied crystal display) (33)
   i. RFDU status light (34)
   j. RFDU entry/exit sensors (35)
3. RFSU-1 (radiofrequency sanitization unit 1—see FIGS. 4 and 5). The main building blocks of RFSU-1 are:
   a. PCB for RFSU 1 (14) [embedded in faucet (48)]
   b. RFSU-1 faucet (48)
   c. RFSU-1 LCD (liquefied crystal display) (50)
   d. RFSU-1 microcontroller (72)
   e. RFSU-1 motion sensor (54)
   f. RFSU-1 motion detector (56)
   g. RFSU-1 cleaning substance dispenser spout (58)
   h. RFSU-1 water spout (60)
   i. RFSU-1 battery charger (62)
   j. RFSU-1 radiofrequency circuit (64)
   k. RFSU-1 battery (66)
   l. RFSU-1 data base (68)
   m. RFSU-1 interface (70)
   n. RFSU-1 speaker (52)
   o. RFSU-1 power supply (74)
   p. RFSU-1 cleaning substance dispenser (76)
   q. RFSU-1 electric valve (78)
   r. RFSU-1 tankless water heater (80)
   s. RFSU-1 could, optionally, as described below in the Preferred embodiment #2, be equipped with a Distance Ranger which, in combination with the Motion Detector (56), could monitor the specific hand rubbing techniques required by the Centers for Disease Control and Prevention (CDC) and the World Health Organization (WHO).
4. RFSU-2 (radiofrequency sanitization unit 2—see FIG. 6) (optional). The main building blocks of RFSU-2 are:
   a. PCB for RFSU 2 (radiofrequency sanitization unit 2)(16)
   b. RFSU-2 LCD (liquefied crystal display)(82)
   c. RFSU-2 battery charger (84)
   d. RFSU-2 battery (86)
   e. RFSU-2 radiofrequency circuit (88)
   f. RFSU-2 cleaning substance dispenser (92)
   g. RFSU-2 motion sensor (94)
   h. RFSU-2 motion detector (96)
   i. RFSU-2 interface (98)
   j. RFSU-2 microcontroller (100)
   k. RFSU-2 data base (102)
   l. RFSU-2 speaker (104)
   m. RFSU-2 could, optionally, as described below in the Preferred embodiment #2, be equipped with a Distance Ranger which, in combination with the Motion Detector (56), could monitor the specific hand rubbing techniques required by the Centers for Disease Control and Prevention (CDC) and the World Health Organization (WHO).

Preferred Embodiment #1

The preferred embodiment #1 monitors proper hand washing in an entire business entity. Examples of business entities in need of monitoring hand washing would be hospitals, food processing plants, hotels, restaurants, and many others. The preferred embodiment #1 consists of six main units. The first four units are identical to the four units described in the Alternative embodiment above, i.e. RFID (see item 1 above), RFDU (see item 2 above), RFSU-1 (see item 3 above), RFSU-2 (see item 4 above), and the last two units are listed below:

5. RFCU-1 (radiofrequency contamination unit 1—see FIG. 7). The main building blocks of RFCU-1 are:
   a. PCB of RFCU-1 (radiofrequency contamination unit 1)(18)
   b. RFCU-1 radio frequency circuit (106)
   c. RFCU-1 battery (108)
   d. RFCU-1 battery charger (110)
   e. RFCU-1 data base (112)
   f. RFCU-1 microcontroller (114)
6. RFCU-2 (radiofrequency contamination unit 2—see FIG. 8). The main building blocks of RFCU-2 are:
   a. PCB of RFCU-2 (radiofrequency contamination unit 2) (20)
   b. RFCU-2 radiofrequency circuit (116)
   c. RFCU-2 battery (118)
   d. RFCU-2 battery charger (120)
   e. RFCU-2 data base (122)
   f. RFCU-2 microcontroller (124)

Preferred Embodiment #2

The main units of the Preferred Embodiment #2, as well as the main building blocks of the units of the Preferred Embodiment #2, are the same as the ones of the Preferred Embodiment #1 (see FIGS. 1,2,3,4,5,6,7, and 8), except that:

1. RFCU-1 of the Preferred Embodiment #1 is replaced by two units in the Preferred Embodiment #2:
   a. RFBU (radiofrequency bed unit), attached proximal to a patient, whose main building blocks are identical to the RFCU-1 of the Preferred Embodiment #1 (see FIG. 7), and
   b. RFPU (radiofrequency patient unit), attached to a patient, whose main building blocks are identical to the RFID of the Preferred Embodiment #1 (see FIG. 2)
2. Preferred Embodiment #2 utilizes the Motion Sensor (56), attached to RFSU-1, and 2, for detecting the presence of hands, and a Distance Ranger, attached to RFSU-1, and 2, which detects the distance between said ranger and the hands, for the purpose of monitoring the specific hand rubbing techniques required by the Centers for Disease Control and Prevention (CDC) and the World Health Organization (WHO).

Operation

Alternative Embodiment

The Alternative embodiment is an electronic hand-washing monitoring system that will be installed at restroom areas in food and healthcare facilities, such as restaurants and hospitals, as well as any other facility, which requires monitoring of hand washing after using a restroom. The system uses RF (radiofrequency) identification technology to establish communication between its three main units as well as the optional unit. The system also uses embedded microcontrollers to achieve its control functionality. The main database including the individual's specific data is maintained in a central computer and gathered from the various monitoring systems within the building via RF data transfer technology. Data is communicated to the users via backlit LCD display and voice prompts.

The system of this embodiment comprises the following main units as depicted in FIG. 1:
1. RFID (radiofrequency identification unit). Each employee wares his/her own unique RFID badge which holds the identification information about the employee and his/her recent history of hygiene compliance.
2. RFDU (radiofrequency door unit) (12). This unit is mounted at the entrance of each restroom facility within a facility, such as a restaurant, or a hospital, or others. Its primary function is to detect the employee at each entry and exit to and from the restroom. It visually and audibly alerts the employee at the exit if he/she did not get engaged with the hand washing enforcement process at the faucet, RFSU.
3. RFSU-1 (radiofrequency sanitization unit 1) (14). This unit is embedded within the faucet assembly and is capable of identifying the employee when he/she approaches the faucet to wash his/her hands, of engaging said employee in the hand washing process, of detecting if said employee successfully completed the hand washing process, of visually and audibly alerting said employee of his/her pass/fail status, and of stamping the RFID of said employee with said pass/fail status. Monitoring of the hand washing process consists of monitoring the dispensation of cleaning substance, the duration of hand rubbing, and the duration of hand rinsing through the use RFSU-1 motion sensor (54) and RFSU-1 motion detector (56).
4. RFSU-2 (radiofrequency sanitization unit 2) (16) is an optional unit with very similar functionality to the RFSU-1 (see FIG. 6). The main difference between the two units is that RFSU-2 uses hand cleansing substances that do not require running water for rinsing them off, like alcohol based cleansers. All other functions are identical to RFSU-1. In most, but not all, instances the use of RFSU-2 is allowable instead of the use of RFSU-1. Monitoring of the hand cleaning process consists of monitoring the dispensation of cleaning substance, and the duration of hand rubbing, through the use RFSU-2 motion sensor (94) and RFSU-2 motion detector (96).

The RFID (radiofrequency identification unit) is the employee badge which must be worn all the time during working hours. It emits detectable RF waves within a radius of two feet or so and has the size of a name tag or a credit card. The RFID holds the employee name and his/her history of all visits to the restrooms. The RFID consists of the following components as shown in FIG. 2:
1. RFID microcontroller (24).
2. RFID database (28) to store the hygiene history of the employee.
3. RFID radiofrequency circuit (28) with transceiver and embedded antenna.
4. RFID tri-color status light (26), flashing orange (in the rest room), alternating green/red (engaged with RFSU), flashing green (passed), and flashing red (failed).
5. RFID battery (30) with one-year life span.

The functionality and capability of the RFID:
a. Communicates with the RFDU at every entry to get time-stamped.
b. It keeps the time while within the restroom
c. Communicates with the RFSU to acknowledge the employee's engagement with the hand washing process.
d. It receives the pass/fail status of compliance from the RFSU and keeps it.
e. Communicates with the RFDU at each exit and reports the pass/fail status.
f. The RFID badge itself is the communication link between the RFSU (sanitization, or wash station, unit) and the RFDU (door unit). This approach is important so that we keep all three RF transceivers, RFID, RFDU, and RFSU at a minimum transmission power of detectable RF waves within a radius of two feet or so. This way we avoid various systems from interfering with each other if they are too close, such as two bathrooms on two different floors but the same vertical position.

The RFDU (radiofrequency door unit) (12) is the main control device, which is mounted inside the wall close to the restroom entrance door frame in an enclosure of the size of an electric box. It emits detectable RF waves within a radius of two feet or so. It is normally off and gets turned on by the normally on entry/exit sensors (35), which allows the employee's RFID to communicate with it any time said employee enters or exits the restroom. The RFDU keeps the hygiene history file for all employees who have engaged it until the time this history file is uploaded to the company's main computer(s) for the management to review. The RFDU comprises the following components as shown in FIG. 3:
1. RFDU microcontroller (46).
2. RFDU database (42) to store the hygiene history of all employees, who enter the restroom.
3. RFDU radiofrequency circuit (38) with a transceiver and an internal antenna to communicate with the RFID
4. RFDU upload link (44) to upload the data to the company's main computer. This could be of any possible form, USB, Ethernet, Phone, or wireless.
5. RFDU LCD (liquefied crystal display) (33). Large backlit LCD to display names and the appropriate message of welcoming at each entrance or appreciation/warning at each exit.
6. RFDU speaker (32). A speaker for added audible messaging.
7. RFDU tri-color status light (34), flashing orange (some employees in the rest room), flashing green (exiting employee passed), and flashing red (exiting employee failed).
8. RFDU battery (40). AC-powered with an automatic charger and a backup battery with one-month life.
9. RFDU entry/exit sensors (35). RFDU entry/exit sensors (35) are constantly on. Turns the RFDU on any time an employee enters or exits the restroom, so that RFID and RFDU can exchange information about compliance or noncompliance with the hand washing requirements.

The functionality and capability of the RFDU (12)
a. Detects the employee's RFID at every entry to welcome the employee by name (LCD & speaker).
b. Communicates with the RFID at each exit to get the pass/fail status of the employee and immediately generate message of either appreciation for compliance or warning otherwise.
c. Keeps a real-time log of all entries, exits, and hygiene history of all employees, who have engaged it.
d. Uploads history files to the company's main computers.

The RFSU-1 (radiofrequency sanitization unit 1) (14) is the unit the employee engages to wash his/her hands. It is normally off and gets turned on by the RFSU-1's motion sensor (54), which is normally on, any time an employee approaches it and puts his hand under the faucet for cleansing substance dispensation. It emits detectable RF waves within a two feet radius or so and comprises a faucet assembly, which houses the water spout (60), the cleansing substance spout (58), the motion sensor (54), and motion detector (56), and the following components (see FIGS. 4 and 5):
1. RFSU-1 microcontroller (72).
2. RFSU-1 database (68). Used to temporary store the monitored washing activities.
3. RFSU-1 radiofrequency circuit (64). Transceiver and internal antenna to communicate with the RFID.
4. RFSU-1 interface (70). Interface circuit to control external peripherals like the cleaning substance dispenser (76), the water valve (78), the motion detector (56), and any future input/output devices.
5. Large back-lit LCD to display the name of the engaged person and the steps of the hand washing process.
6. A speaker for added audible messaging.
7. AC-powered and automatic charger with a backup battery of one-month life.
8. RFSU-1 motion sensor (54). RFSU-1's motion sensor (54) is normally on. It has the dual function of turning the RFSU-1 on any time an employee puts his/her hand under the faucet for dispensation of cleansing substance as well as the function of triggering dispensation of cleansing substance.
9. RFSU-1 motion detector (56). RFSU-1 motion detector monitors the hand rubbing motion during the hand washing process. It continues the hand rubbing countdown while hand rubbing motion is detected, and stops the countdown if no motion is detected. If no motion is detected for more than 10 seconds at a time, RFSU-1 resets.

The functionality and capability of the RFSU-1:
a. Detects the employee's RFID (name, time stamps) as soon as the employee puts his hand under the faucet. That engages the motion sensor (54), which is constantly on and in turn turns the RFSU-1 on and gives a command to the cleaning substance dispenser (76) to dispense cleaning substance on the employee's hand. The RFSU-1 interrogates the RFID every second until the employee completes the hand washing sequence.
b. The RFSU-1 welcomes the employee by name (LCD & speaker) and walks him/her through the washing sequence, which is dispensing soap, rubbing hands while providing trickling water flow for achieving proper cleaning substance consistency, and rinsing under full water flow, all of them for programmable durations displayed for the employee on countdown timers.
c. Communicates with the RFID at the end of washing process to stamp it with pass/fail status.
d. If the washing sequence is not completed, the engaged RFID is stamped with a fail status.
e. Generates the appropriate messages, either appreciating compliance or warning otherwise.
f. One of the most vital aspects accomplished by the RFSU-1 is the enforcement part, which requires that the system monitors the actual hand washing sequence. Hands have to be rubbed for a period of 20 seconds after dispensation of cleansing substance. Monitoring of that activity is being achieved by the use of the RFSU-1's motion detector (56), which will stop the 20 sec. countdown whenever hand rubbing motion is not being detected. Also, histograms of repetitive motions, which could be used to defeat this feature, have been eliminated from the countdown timing of the hand rubbing. During the 20 sec. of hand rubbing activity the water will flow at a slow, trickle flow, rate for diluting the cleaning substance solution, if necessary, and as soon as the countdown is completed the water will start flowing at a normal rate for rinsing the cleansing substance off of one's hands.

The RFSU-2 (radiofrequency sanitization unit 2) (16) is an optional unit with very similar functionally to the RFSU-1 (see FIG. 6). The main difference between the two units is that the RFSU-2 uses hand cleansing substances that do not require running water for rinsing them off, like alcohol based cleansers. All other functions are identical to RFSU-1. In most, but not all, instances the use of RFSU-2 is allowable instead of the use of RFSU-1.

An example of a detailed algorithm, among many others, that achieves as an end result proper monitoring of employees' hand washing by using the Alternative embodiment is shown on FIG. 9

Preferred Embodiment #1

The preferred embodiment monitors proper hand washing in an entire business entity. Examples of business entities in need of monitoring hand washing would be hospitals, food processing plants, hotels, restaurants, and many others. The preferred embodiment #1 consists of six main units. The first four units are identical to the four units described in the Alternative embodiment above, i.e. RFID (see description above), RFDU (see description above), RFSU-1 (see description above), and RFSU-2 (see description above). RFID in the Primary embodiment #1 retains all the hand washing information of the person who wears it throughout his/her working day and then it transfers it to the RFDU on the way out of work. The last two units of the preferred embodiment #1 are RFCU-1, and RFCU-2:

RFCU-1 (radiofrequency contamination unit-1—see FIG. 7). RFCU-1 warns the person wearing the RFID that he/she must wash his/her hands within 10 seconds before engaging it and within 10 seconds after disengaging it. It allows more than one person to engage it at the same time. RFCU-1 must be attached proximal to any person or object that must be dealt with clean hands. A perfect example of the use of RFCU-1will be its attachment proximal to a patient in order to ensure that said patient is being engaged by a person who has washed his/her hands within the previous 10 seconds. It emits detectable RF waves within a radius of two feet or so and comprises the following components as shown on FIG. 7:
1. PCB of RFCU-1 (Radio Frequency Contamination Unit-1) (18)
2. RFCU-1 radiofrequency circuit (106). Utilizes RF transceiver and internal antenna to communicate with the RFID.
3. RFCU-1 battery (108). AC-powered with or without battery charger as needed.
4. RFCU-1 battery charger (110). Battery charger could be used if attached to an object.
5. RFCU-1 data base (112). Used to store hygiene information, on a temporary bases, of all employees, who engage it.
6. RFCU 1 microcontroller (114)

The functionality and capability of the RFCU-1:
a. Detects the employee's RFID as soon as the RFID is within the sphere of engagement of RFCU-1.
b. Approves of the engagement with the RFID if the employee has washed his/her hands within 10 seconds before engaging it and warns said employee to wash his/her hands within 10 seconds after disengaging it.
c. Allows more than one person to engage it as long as said person(s) has washed his/her hands within 10 seconds before engaging it.

d. Keeps a real time log of all engagements for the last thirty days.

e. RFCU-1 could be used together with entry/exit sensors (35) of the alternative embodiment to monitor compliance with hand washing in restrooms. RFCU-1 would normally be off. The entry part of the entry/exit sensors (35) will not turn it on, so that the employees entering the restroom could enter undetected and unregistered. The exit part of the entry/exit sensors (35), however, will turn the RFCU 1 when the employee is exiting the restroom and, if the employee has not washed his/her hands within the previous 10 seconds as required, a default will be registered on his/her behalf.

RFCU-2 (radiofrequency contamination unit-2—see FIG. 8). RFCU-2 emits detectable RF waves within a radius of two feet or so. RFCU-2 allows anybody to engage it, but warns the person wearing the RFID to use an RFSU to wash his/her hands within 15 seconds after disengaging it. It allows more than one person to engage it at the same time if the contaminated objects, like urinals, are in close proximity. Examples of using RFCU-2s could be toilet bowls, urinals, contaminated equipment, etc. RFCU-2 comprises the following components, as shown on FIG. 8:

1. PCB of RFCU 2 (radiofrequency contamination unit-2) (20)
2. RFCU-2 radiofrequency circuit (116). Utilizes RF transceiver and internal antenna to communicate with RFID.
3. RFCU-2 battery (118). AC-powered with automatic charger and a battery of one month life.
4. RFCU-2 battery charger (120)
5. RFCU-2 data base (122). Used to store hygiene information on a temporary basis of all employees, who engage it.
6. RFCU 2 microcontroller (124)

The functionality and capacity of RFCU-2:

a. Detects the employee's RFID as soon as the employee moves into the sphere of coverage of RFCU-2.
b. Interrogates the RFID every second for the duration its engagement with RFCU-2.
c. At the moment of disengagement with RFID advises employee he/she must wash his/her hands at an RFSU within the next 15 seconds.
d. Keeps a real time log of all engagements for the last thirty days.

Preferred Embodiment #2

The preferred embodiment #2 of the SaniFaucet Hand Washing Enforcement System is almost identical to the preferred embodiment #1, described above. The main differences are described below:

1. In the preferred embodiment #1 all the hand washing information throughout the working day is being gathered and stored in the memory chip of the RFID, and at the end of the day that information is transferred to the RFDU for further reporting to the computer database, while in the preferred embodiment #2 the RFID transfers wirelessly, real time, all the hand washing activities of its bearer to the computer database by updating its status instantaneously as it changes (see sub-item 3. below).

2. RFCU-1 of the preferred embodiment #1 is being replaced in the preferred embodiment #2 by two units—RFPU (Radiofrequency Patient Unit), attached to any patient in healthcare facilities, and RFBU (Radiofrequency Bed Unit), attached proximal to a patient, and moved with the patient while the patient is away from his/her bed. The RFPU and the RFBU have to be in close proximity to each other, and in constant communication with each other at all times in order to provide uninterrupted protection to the patient from being engaged by a person with unclean hands. The RFBU acts like RFCU-1 of preferred embodiment #1, and detects any person coming in close proximity to the patient, assuring that said person has washed his/her hands within the previous 10 seconds. In addition to RFCU-1's functionalities with the Preferred embodiment #1, however, the RFBU is in constant communication with RFPU in order to update RFPU's status instantaneously as it changes (see item 3. below). The RFPU reports its own status (see item 3. below) to the computer database, just like any RFID does. It determines its own status by being in constant communication with the RFBU.

3. Reporting data to the computer database in Embodiment #2 is streamlined better by the addition of statuses, assigned to all hand washing activities, for the RFIDs and RFPUs. RFID statuses in the preferred embodiment #2 range from being clean while its bearer is exiting a restroom, to being freshly clean while outside a restroom, being with normal status, being engaged with a patient, being engaged with an RFCU-2, and being in default.

RFPU is attached to a patient. Its statuses range from the patient is in bed alone to the patient is being treated, and the patient is away from his/her bed.

4. The hand rubbing process in the preferred embodiment #1 is being monitored by a motion detector (56), which detects only if there is motion or not, while the hand rubbing process in the preferred embodiment #2 is being monitored by the motion sensor (56) for detecting the presence of hands, and a Distance Ranger which detects the distance between the ranger and the hands. During the course of the hands motion, the distance is sampled many times, say a 100 times per second. Then the data is plugged into a histogram and analyzed for repeated patterns. The data is compared dynamically to pre-sorted various patterns of hand-washing histograms. If the actual pattern is within an acceptable tolerance of the stored pattern, then the hand rubbing, as well as the hand-washing, is considered good.

The stored patterns will be based on a poster of required hand rubbing techniques, published by the Centers for Disease Control and Prevention (CDC) and the World Health Organization (WHO), which could be found on the Internet at the following link:

http://www.who.int/gpsc/5may/How_To_HandRub_Poster.pdf which namely includes the steps of: (1a) and (1b) Apply a palmful of the product in a cupped hand, covering all surfaces; (2) rub hands palm to palm; (3) right palm over left dorsum with interlaced fingers and vice versa; (4) palm to palm with fingers interlaced; (5) backs of fingers to opposing palms with fingers interlocked; (6) rotational rubbing of left thumb clasped in right palm and vice versa; (7) rotational rubbing, backwards and forwards with clasped fingers of right hand in left palm and vice versa; (8) once dry, your hands are safe.

A simplified and less detailed but more graphic way of describing the SaniFaucet Hand Washing Enforcement System (aka Golden Faucet Hand Washing Enforcement System) would be by picturing a mobile beacon(s) [RFID(s)—radiofrequency identification unit(s)], emitting RF (radiofrequency) waves of two feet in radius or so, moving among stationary beacons [RFCUs—radiofrequency contamination units; RFSUs—radiofrequency sanitization units; RFDU(s)—radiofrequency door unit(s)], emitting RF waves of two feet in radius or so, and by entering said stationary beacons' spheres of engagement, either by chance or design, and communicating with them said mobile beacon(s) makes a determination when hand washing is necessary. Then, after collecting and retaining all hand washing information throughout the working day, said mobile beacon(s) transfers said hand washing information at the end of the working day to the RFDU (radio frequency door unit) on the way out of work. The information received by the RFDU(s) from all RFIDs could be transferred real time, or through an USB unit, or through any other available technical means to a central data base for the management to review.

CONCLUSIONS, RAMIFICATIONS AND SCOPE

Accordingly, the reader will see that my invention is one whose time has come. When it becomes codified nationwide, and abroad, it will prevent millions of deaths, and it will reduce tremendously the spread of infectious diseases and the cost associated with it. Said cost, as I wrote earlier, is estimated to be in excess of 40 billion dollars per year in the United States alone.

While I listed only three embodiments, I could think of quite a few more, which could be just as good or better, if engineered well with the help of professionals working for any particular enterprise in different industries and with different needs.

What is claimed is:

1. A hand washing enforcement system for at least one individual operative within a predetermined establishment, said system comprising:
    a central computer including a main database,
    at least one radio frequency identification unit (RFID) carried by the individual and movable therewith,
    at least one radio frequency sanitation unit (RFSU) associated with a washing station and structured to monitor a hand washing process of the individual and communicate exclusively with said RFID and the individual,
    said RFID structured to render data corresponding to hand washing activities based on hand washing information communicated from said RFSU and disposed to communicate said data to said central computer,
    said RFID further structured to determine an existence of the individual within said sphere of engagement of an occupant and to determine a status of the hand washing practice of the individual,
    said central computer structured to receive said data exclusively from said RFID,
    a radio frequency bed unit (RFBU) disposed proximal to the occupant of the predetermined establishment and within a sphere of engagement of the occupant, and
    at least one radio frequency patient unit (RFPU) attached and movable with the occupant of the predetermined establishment and structured for communication with said central computer and transfer of occupant status to said main database.

2. A system as recited in claim 1 wherein said RFID is further structured for real-time communication of said data to said central computer.

3. A system as recited in claim 1 wherein said data comprises at least a pass/fail status of the individual.

4. A system as recited in claim 1 wherein said occupant status comprises at least occupant location.

5. A system as recited in claim 1 wherein said occupant status further comprises interaction of the individual and the occupant.

6. A system as recited in claim 1 wherein said RFBU and said RFPU are structured for communication with one another within said sphere of engagement.

7. A system as recited in claim 1 wherein said RFSU comprises a distance ranger disposed and structured to determine the distance of the individual's hands relative to said washing station.

8. A system as recited in claim 7 wherein said distance ranger is further disposed and structured to determine performance by the individual of a preferred hand rubbing process.

9. A system as recited in claim 8 wherein said preferred hand rubbing process comprises substantial compliance with hand rubbing technique published by recognized regulatory agencies.

10. A system as recited in claim 9 wherein said preferred hand rubbing process comprises the steps of:
    applying a palmful of hand washing product in a cupped hand, covering all surfaces,
    rubbing hands palm to palm,
    rubbing hands right palm over left dorsum with interlaced fingers, and vice versa,
    rubbing hands palm to palm with fingers interlaced,
    rubbing hands with backs of fingers to opposing palms, with fingers interlocked,
    rubbing left thumb rotationally clasped in right palm, and vice versa, and
    rubbing clasped fingers of right hand in left palm rotationally, backwards and forwards, and vice versa.

11. A system as recited in claim 1 wherein said RFSU further comprises a motion sensor disposed and structured to determine an existence of the individual's hands at said washing station.

12. A system as recited in claim 1 wherein the said RFSU is programmable to establish predetermined time duration of performance of said washing process including at least said preferred rubbing process of the individual's hands with a cleansing composition.

13. A system as recited in claim 12 wherein said compliance with said washing process, monitored by said RFSU, comprises dispensing of water and cleansing composition, rubbing of the individual's hands with said cleansing composition and rubbing of the individual's hands while rinsing said cleansing composition with water.

14. A hand washing enforcement system for at least one individual operative within a predetermined establishment, said system comprising:
    at least one radio frequency identification unit (RFID) carried by the individual and movable therewith;
    a central computer including a main database;
    at least one radio frequency sanitation unit (RFSU) associated with a washing station and structured to monitor a hand washing process of the individual, and further structured to exclusively communicate with said RFID and the individual;
    said RFID structured to render hand washing activity data based on hand washing activities communicated from said RFSU;
    said central computer structured for communication of said hand washing activity data exclusively with said RFID;
    at least one of a radio frequency door unit (RFDU) fixedly mounted adjacent a predetermined area and structured to transmit data to said RFID; and
    at least one radio frequency patient unit (RFPU) attached and movable with an occupant of the predetermined establishment, and structured for communication with said central computer and transfer of occupant status to said main database.

15. A system as recited in claim 14 wherein said data comprising at least a pass/fail status determined by compliance with said hand washing process.

16. A system as recited in claim 14 wherein said RFSU comprises a motion sensor disposed and structured to determine an existence of the individual's hands at said washing station.

17. A system as recited in claim 14 wherein said RFSU further comprises a distance ranger disposed and structured to determine distance of the individual's hands relative to said washing station.

18. A system as recited in claim 17 wherein said distance ranger is further structured to develop a histogram of performance by the individual of said hand washing process.

19. A system as recited in claim 14 wherein said hand washing process comprises substantial compliance with hand rubbing technique published by recognized regulatory agencies.

20. A system as recited in claim 19 wherein said hand washing process comprises the steps of:
   applying a palmful of hand washing product in a cupped hand, covering all surfaces,
   rubbing hands palm to palm,
   rubbing hands right palm over left dorsum with interlaced fingers, and vice versa,
   rubbing hands palm to palm with fingers interlaced,
   rubbing hands with backs of fingers to opposing palms, with fingers interlocked,
   rubbing left thumb rotationally clasped in right palm, and vice versa, and
   rubbing clasped fingers of right hand in left palm rotationally, backwards and forwards, and vice versa.

21. A system as recited in claim 14 further comprising a radio frequency bed unit (RFBU) disposed proximal to the occupant of the predetermined establishment and within a sphere of engagement of the occupant.

22. A system as recited in claim 21 wherein said occupant status comprises at least occupant location.

23. A system as recited in claim 22 wherein said occupant status further comprises interaction of the individual and the occupant.

24. A system as recited in claim 23 wherein said RFBU and said RFPU are structured for communication with one another within said sphere of engagement.

* * * * *